United States Patent
Murto et al.

(10) Patent No.: US 10,945,959 B2
(45) Date of Patent: *Mar. 16, 2021

(54) SYSTEM AND METHOD FOR FREEZE-DRYING AND PACKAGING

(71) Applicant: Teleflex Life Sciences Limited, Valletta (MT)

(72) Inventors: James A. Murto, Maple Grove, MN (US); Stephen Anthony Penegor, Watertown, MN (US)

(73) Assignee: Teleflex Life Sciences Limited, Valletta (MT)

( * ) Notice: Subject to any disclaimer, the term of this patent is extended or adjusted under 35 U.S.C. 154(b) by 0 days.

This patent is subject to a terminal disclaimer.

(21) Appl. No.: 16/295,165

(22) Filed: Mar. 7, 2019

(65) Prior Publication Data

US 2020/0281858 A1    Sep. 10, 2020

(51) Int. Cl.
| | |
|---|---|
| *A61K 9/19* | (2006.01) |
| *A61B 5/15* | (2006.01) |
| *A61K 9/00* | (2006.01) |
| *A61K 35/16* | (2015.01) |
| *F26B 5/06* | (2006.01) |

(52) U.S. Cl.
CPC .......... *A61K 9/19* (2013.01); *A61B 5/150755* (2013.01); *A61K 9/0026* (2013.01); *A61K 35/16* (2013.01); *F26B 5/06* (2013.01); *A61K 2236/51* (2013.01)

(58) Field of Classification Search
CPC .. A61K 9/19; A61K 35/16; A61B 5/15; F26B 5/06
See application file for complete search history.

(56) References Cited

U.S. PATENT DOCUMENTS

| | | | |
|---|---|---|---|
| 4,024,648 A | 5/1977 | Bender | |
| 4,335,770 A | 6/1982 | Kulle et al. | |
| 4,453,320 A | 6/1984 | Zimmermann et al. | |
| 4,707,966 A * | 11/1987 | Weiler | B29C 65/56 264/524 |
| 4,813,210 A | 3/1989 | Masuda et al. | |
| 4,994,057 A | 2/1991 | Carmen et al. | |
| 5,174,042 A | 12/1992 | Tomizawa et al. | |
| 5,309,649 A | 5/1994 | Bergmann et al. | |
| 5,514,123 A | 5/1996 | Adolf et al. | |
| 5,596,814 A | 1/1997 | Zingle et al. | |
| 5,894,949 A * | 4/1999 | Taskis | B65D 51/30 215/247 |
| 5,937,536 A | 8/1999 | Kieselbach et al. | |
| 5,958,778 A | 9/1999 | Kidd | |
| 6,375,028 B1 * | 4/2002 | Smith | B01L 3/50825 215/278 |
| 6,381,870 B1 | 5/2002 | Kohlman et al. | |
| 6,517,526 B1 | 2/2003 | Tamari | |
| 6,764,481 B1 | 7/2004 | Inada et al. | |
| 6,773,425 B1 | 8/2004 | Tamari | |
| 6,981,337 B2 | 1/2006 | Jones et al. | |
| 7,363,726 B2 | 4/2008 | Wang et al. | |
| 7,776,022 B2 | 8/2010 | McCarthy et al. | |
| 7,966,746 B2 | 6/2011 | Py | |
| 8,013,022 B2 | 9/2011 | DeAngelo et al. | |
| 8,076,034 B1 | 12/2011 | Lassila et al. | |
| 8,449,520 B2 | 5/2013 | Pepper et al. | |
| 8,512,428 B2 | 8/2013 | Ueki et al. | |
| 8,518,452 B2 | 8/2013 | Bjornstrup et al. | |
| 8,555,520 B2 | 10/2013 | Hedberg | |
| 9,347,707 B2 | 5/2016 | Struschka et al. | |
| 9,561,893 B2 | 2/2017 | Root et al. | |
| 9,739,532 B2 | 8/2017 | Baugh et al. | |
| 9,796,273 B2 | 10/2017 | Ragazzini | |
| 9,801,784 B2 | 10/2017 | Yoshida et al. | |
| 9,863,699 B2 | 1/2018 | Corbin et al. | |
| 9,863,700 B2 | 1/2018 | Pedersen et al. | |
| 9,863,701 B2 | 1/2018 | Robinson | |
| 9,931,458 B1 | 4/2018 | Naro | |
| 10,300,444 B2 | 5/2019 | Prytz | |
| 10,377,520 B2 | 8/2019 | Root et al. | |
| 10,806,665 B2 | 10/2020 | Murto et al. | |
| 10,882,654 B2 | 1/2021 | Root et al. | |
| 2008/0234654 A1 | 9/2008 | McCarthy et al. | |
| 2008/0256822 A1 | 10/2008 | Suzuki et al. | |
| 2009/0107001 A1 | 4/2009 | McCarthy | |
| 2009/0113753 A1 | 5/2009 | Pepper et al. | |
| 2009/0325771 A1 | 12/2009 | Inoue et al. | |
| 2014/0360891 A1 | 12/2014 | Kline et al. | |
| 2015/0158652 A1 | 6/2015 | Root et al. | |
| 2015/0231031 A1 | 8/2015 | Hayakawa et al. | |

(Continued)

FOREIGN PATENT DOCUMENTS

| | | |
|---|---|---|
| CN | 203284363 U | 11/2013 |
| DE | 102013003851 | 3/2014 |

(Continued)

OTHER PUBLICATIONS

European Search Report dated Jul. 17, 2020 in European Application No. 20159141.9.

*Primary Examiner* — Shirley V Gembeh

(74) *Attorney, Agent, or Firm* — Christopher J. Buchko; Gregory W. Smock

(57) ABSTRACT

A system and method for freeze-drying a heat-sensitive substance. In some embodiments, the system and method include freeze-drying the heat-sensitive substance in an upright container with a membrane for transmitting air or vapor solvent out of the container.

19 Claims, 8 Drawing Sheets

(56) References Cited

U.S. PATENT DOCUMENTS

| | | |
|---|---|---|
| 2015/0354894 A1 | 12/2015 | Corbin et al. |
| 2017/0113824 A1 | 4/2017 | Root et al. |
| 2017/0203871 A1 | 7/2017 | Murto et al. |
| 2019/0241300 A1 | 8/2019 | Root et al. |

FOREIGN PATENT DOCUMENTS

| | | |
|---|---|---|
| EP | 0854911 B1 | 11/2004 |
| JP | H07165252 A | 6/1995 |
| WO | 1995027180 A1 | 10/1995 |
| WO | 1996006018 A1 | 2/1996 |
| WO | 1996031748 A1 | 10/1996 |
| WO | 2008140747 A1 | 11/2008 |
| WO | 2010033169 A1 | 3/2010 |
| WO | 2015191599 A2 | 12/2015 |

\* cited by examiner

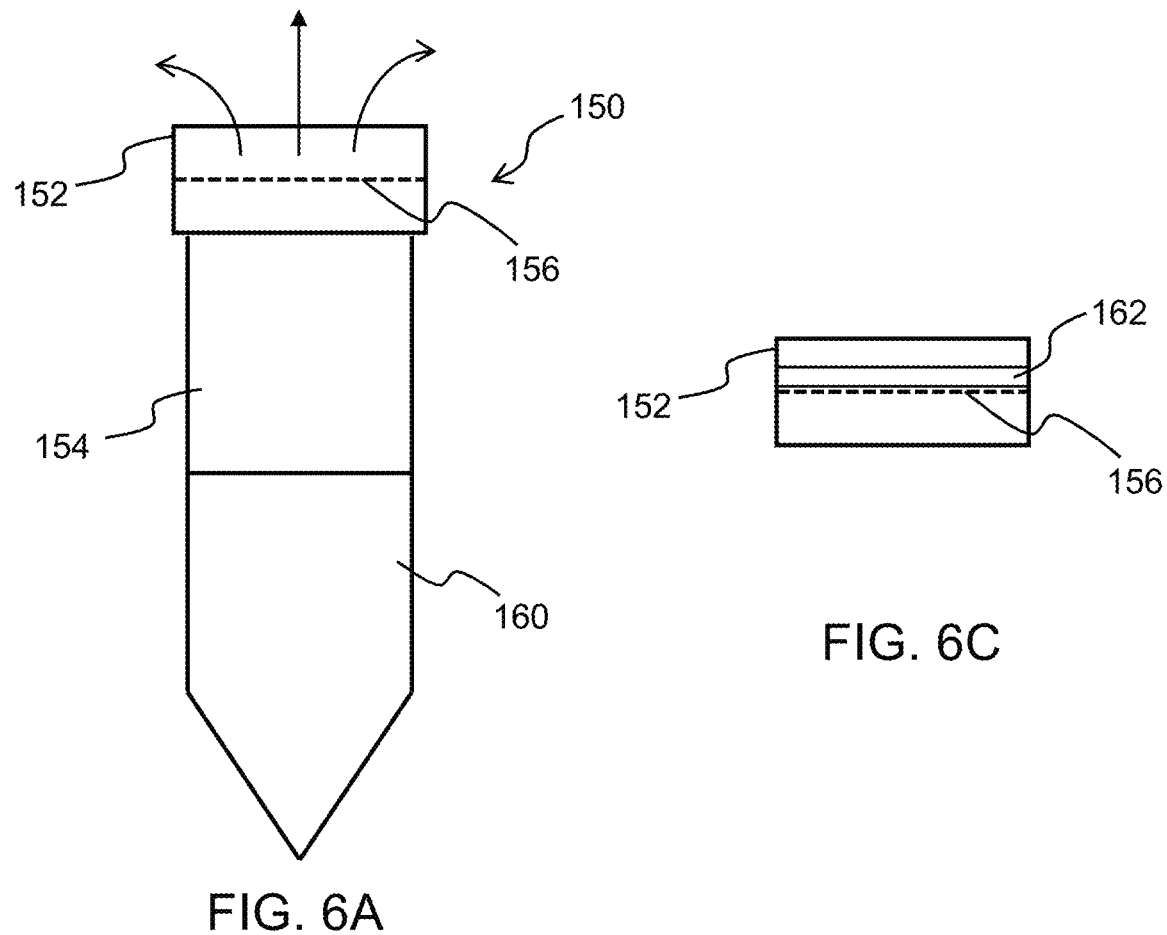
FIG. 6A
FIG. 6C
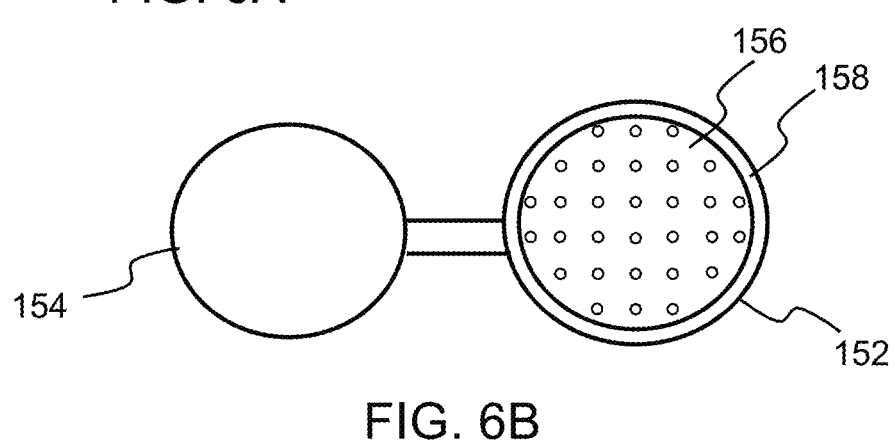
FIG. 6B

SYSTEM AND METHOD FOR FREEZE-DRYING AND PACKAGING

BACKGROUND OF THE INVENTION

The present disclosure relates generally to a lyophilization system and associated method and, in particular, to a system and method for freeze-drying heat-sensitive substances such as biological materials or pharmaceutical formulations under aseptic or contaminant-reduced conditions.

Dry storage can increase the shelf life and convenience of heat-sensitive substances such as, but not limited to, biological materials, pharmaceutical formulations, and therapeutic products including chemical compositions, plasma-derived therapies, and recombinants. Such products can be unstable in solution and require lyophilization, particularly when produced as parenterals. Lyophilization is a process for drying heat-sensitive substances by freezing the substances and then subliming the ice or other frozen solvent in a high vacuum.

It is often necessary to keep heat-sensitive substances sterile and free from microorganisms and other contaminants to avoid decomposition or degradation, and prevent possible infection when the material is introduced into a patient. Heat-sensitive substances can be exposed to contaminants during transportation to and from a freeze-dryer (lyophilizer). As a result, the freeze-drying operating area undergoes sterilization to minimize exposure of the material to contaminants. This effectively increases the labor and costs associated with lyophilization and sterilization.

Many freeze-drying processes involve placing open, or partially stoppered, containers of heat-sensitive substances in a freeze-dryer, such that the containers are exposed to the environment until the freeze-drying process is complete, to allow a path for solvent vapor to be removed from the material. This practice exposes the heat-sensitive material to potential contamination during freeze-drying. To minimize potential contamination, freeze-drying equipment can be sterilized via steam or chemicals before loading each new batch of material to be lyophilized. This too increases labor and costs associated with lyophilization and sterilization.

Additionally, some freeze-drying systems and methods require lyophilized materials to be repackaged and/or re-handled, such as by capping or crimping. This repackaging presents another opportunity to introduce contaminants and increase costs.

The present disclosure addresses the need for a system and method that prevent, or at least reduce, contamination of heat-sensitive substances, such as biological or pharmaceutical material, during filling, freeze-drying, packaging, storage, and use.

SUMMARY OF THE INVENTION

Briefly, and in general terms, the present disclosure is directed towards a system that includes an upright, vertical container and at least one integrated gas-permeable membrane that transmits air or solvent vapor out of the container while preventing entry of contaminants. A method can include filling a vertical container with a heat-sensitive substance, inserting a membrane into the body or cap of the container such that the membrane covers the heat-sensitive substance, and freeze-drying the container to produce a lyophilized material.

Embodiments of the disclosure include a system comprising an upright container comprising a body defined by an upper portion, with an opening formed therein, and a lower portion. A removable cap can be sealably attached to the upper portion of the body and configured to cover the opening. A membrane can be configured to transmit air or solvent vapor out of the upright container while resisting liquid or contaminant passage into the upright container, where the membrane is disposed above a fill line of the upright container. The system can include a membrane frame coupled to the perimeter of the membrane. The membrane frame can attach to the upper portion of the body such that the membrane covers the opening of the upright container. The membrane frame can attach to the top of the body via a lip and groove mechanism or threads. The membrane frame can be inserted into the upper portion of the body or the cap via friction fit, a lip and groove mechanism, or threads. The membrane frame is inserted into the cap of the upright container. The upright container can be a glass lyophilization vial, a conical centrifuge tube, a microcentrifuge tube, or a blood collection tube. The cap can be a screw cap, a snap cap closure, a plug, or a stopper.

Embodiments of the disclosure include a method for freeze-drying a heat-sensitive substance. The method comprises filling a vertical container with the heat-sensitive substance, incorporating a membrane into the vertical container, and lyophilizing the heat-sensitive substance to produce a freeze-dried material, wherein air or solvent vapor is removed from the vertical container through the membrane. The method can comprise using the membrane to prevent contaminants from entering the vertical container during lyophilization. The method can comprise storing the freeze-dried material in the vertical container. The method can comprise reconstituting the freeze-dried material in a solvent to produce a reconstituted product. The reconstituted product can be administered to a human or animal subject via infusion or via injection. The freeze-dried material can be reconstituted by piercing the membrane with a syringe carrying the solvent and dispensing the solvent into the vertical container.

Other features and advantages of the present disclosure will become apparent from the following detailed description, taken in conjunction with the accompanying drawings, which illustrate, by way of example, the principles of the disclosure.

BRIEF DESCRIPTION OF THE DRAWINGS

FIG. 6A is a partially transparent, side view of a vertical container with a membrane integrated into the lid of the container according to an embodiment of the disclosure;

FIG. 6B is a top view of the vertical container and membrane of FIG. 6A;

FIG. 6C is a partially transparent, side view of the lid of FIG. 6A with a cover sealing the membrane;

DETAILED DESCRIPTION OF ILLUSTRATIVE EMBODIMENTS

For the following defined terms, certain definitions shall be applied, unless a different definition is given elsewhere in this patent document.

The terms "a," "an," and "the" are used to include one or more than one, independent of any other instances or usages of "at least one" or "one or more."

The term "or" is used to refer to a nonexclusive or, such that "A or B" includes "A but not B," "B but not A," and "A and B."

All numeric values are assumed to be modified by the term "about," whether or not explicitly indicated. The term "about" generally refers to a range of numbers that one of skill in the art would consider equivalent to the recited value (e.g., having the same function or result). In many instances, the term "about" can include numbers that are rounded to the nearest significant figure.

The recitation of numerical ranges by endpoints includes all numbers and sub-ranges within that range (e.g., 1 to 4 includes 1, 1.5, 1.75, 2, 2.3, 2.6, 2.9, etc. and 1 to 1.5, 1 to 2, 1 to 3, 2 to 3.5, 2 to 4, 3 to 4, 3 to 4.25, etc.).

The term "patient" is intended to include mammals such as for human or veterinary applications.

The term "upright" refers to an object having its main axis or a main part vertically oriented when in an operating condition or use position.

Turning now to the figures, which are provided by way of example and not limitation, the present disclosure is directed to a system and method for freeze-drying a heat-sensitive substance in a vertical container with a membrane for transmitting air or vapor solvent out of the container.

Figure 1:
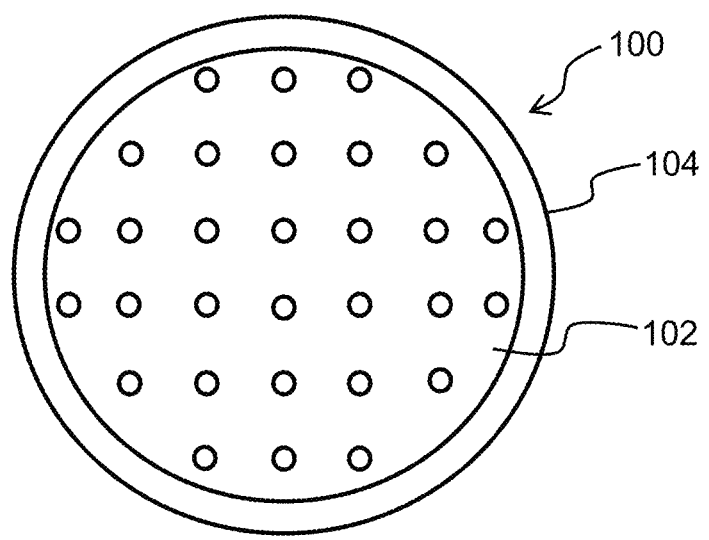
FIG. 1 is a top view of an embodiment of a membrane.
Figure 2:
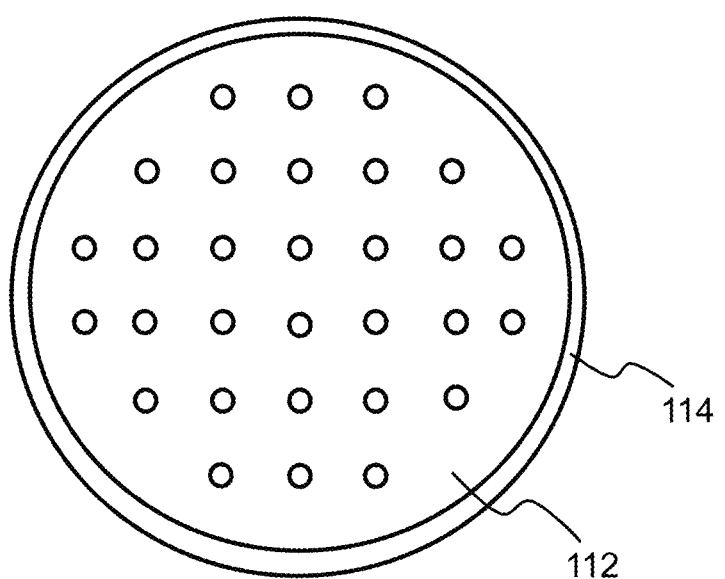
FIG. 2 is a top view of another embodiment of a membrane.

FIGS. 1 and 2 illustrate embodiments of membranes that can be integrated into a container for housing a heat-sensitive material that undergoes a freeze-drying process. Membranes 102 and 112 can be selectively permeable, allowing air or solvent vapor to escape the container during lyophilization while preventing, or at least reducing, entry of liquid and/or contaminants into the container. Membranes 102 and 112 can be made of suitable materials with aseptic barrier properties, high resistance to penetration by moisture or liquids such as water, and low resistance to solvent vapor flow. Such materials can include, but are not limited to, aseptic papers, wove or non-woven polymeric fabrics such as spun-bonded polyolefin, porous polymer membranes such as polytetrafluoroethylene (PTFE) or expanded PTFE, glass fiber, nitrocellulose, mixed cellulose, esters, polyvinylidene fluoride (PVDF), polyethersulfone, polycarbonate, nylon, polypropylene, polyvinyl chloride (PVC), or combinations thereof. In some preferred embodiments, membranes are made of PTFE due to its hydrophobicity and solvent vapor flow for a nominal pore size. While membranes 102 and 112 are circular, it will be understood that the shape of the membrane can be selected to accommodate the shape of a particular container.

As shown in FIG. 1, membrane assembly 100 includes membrane 102 and frame 104 coupled to the perimeter of the membrane. In some embodiments, membrane assembly 100 can be inserted into the neck or upper portion of a container body. In some embodiments, membrane assembly 100 can be inserted or integrated into the cap, lid, plug, or stopper of the container. In some embodiments, membrane assembly 100 can be secured to the opening of the container body. The membrane assembly 100 can be inserted into the body or cap of the container via friction fit, a lip and groove mechanism for snapping in, mating threads for screwing in, or other suitable mechanisms. The membrane assembly 100 faces up when the container body is in the upright position.

In alternative embodiments, such as illustrated in FIG. 2, membrane 112 includes fastening band 114 coupled to the perimeter of the membrane. The underside of the fastening band can contain an adhesive to secure membrane 112 over the opening of a container body.

Membranes can be integrated into variously sized and shaped upright containers including, but not limited to, cosmetic bottles, lyophilization bottles or vials, conical centrifuge tubes, microcentrifuge tubes, vacutainers, blood collection tubes, round bottom centrifuge tubes, test tubes, and/or pouches. Containers can be made from rigid material such as various plastic or glass or from a flexible material. Containers can be self-standing or used in conjunction with a tray or holder. Containers can be transparent and allow for inspection of the heat-sensitive substance prior to, during, and after lyophilization.

Membranes can be incorporated into the container body or cap. Such caps can include, but are not limited to, screw caps, flange plug caps, plug closures, flange cap closures, threaded caps, snap cap closures, hinge caps, and/or stoppers. Caps can be coupled to the body of the container via a hinge or entirely removable. Membranes are oriented such that the transfer of air or solvent vapor out of the container is generally in the vertical direction. That is, the membrane is positioned such that its major surface area is oriented horizontally (i.e., one side of the membrane faces up when the container body is in the upright position).

Figure 3:
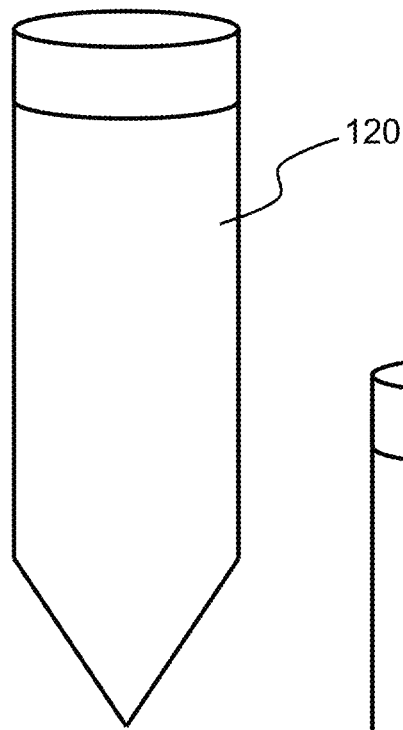
FIG. 3 is a perspective, side view of an embodiment of a vertical container.
Figure 4:
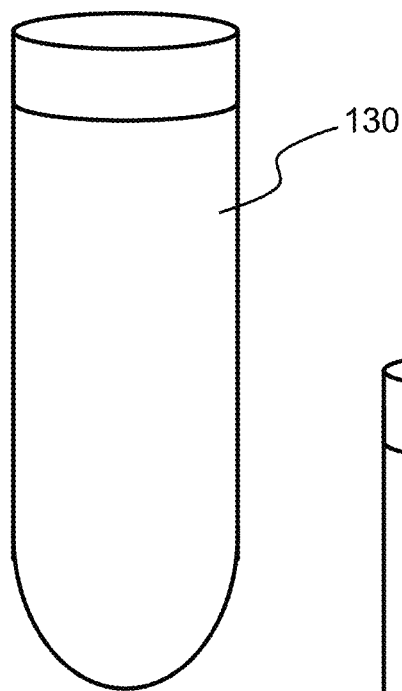
FIG. 4 is a perspective, side view of another embodiment of a vertical container.
Figure 5:
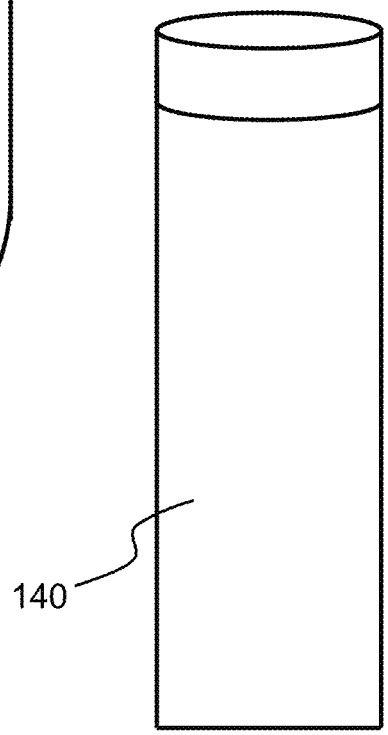
FIG. 5 is a perspective, side view of yet another embodiment of a vertical container.

FIGS. 3-5 illustrate examples of upright containers 120, 130, and 140 that can be used with membranes 102 and/or 112 in a freeze-drying process. Heat-sensitive substances to be freeze-dried can be deposited into the containers prior to lyophilization.

FIGS. 6A, 6B, 6C, 7A, 7B, 8A, and 8B illustrate various integration points (indicated by dashed lines) for a membrane in an upright container. During lyophilization, solvent vapor passes through the membrane and exits the container (indicated by solid arrows), while particulate of the heat-sensitive substance is retained in the container and contaminants are excluded.

As shown in FIGS. 6A, 6B and 6C, container 150 includes body 154 and cap 152. Frame 158 (shown in FIG. 6B) of membrane 156 can be inserted into cap 152. Prior to capping, the interior of body 154 is filled with heat-sensitive substance 160 which subsequently undergoes freeze-drying. Container 150 can optionally include removable cover or insert 162 configured to seal cap 152 after lyophilization.

Figure 7A:
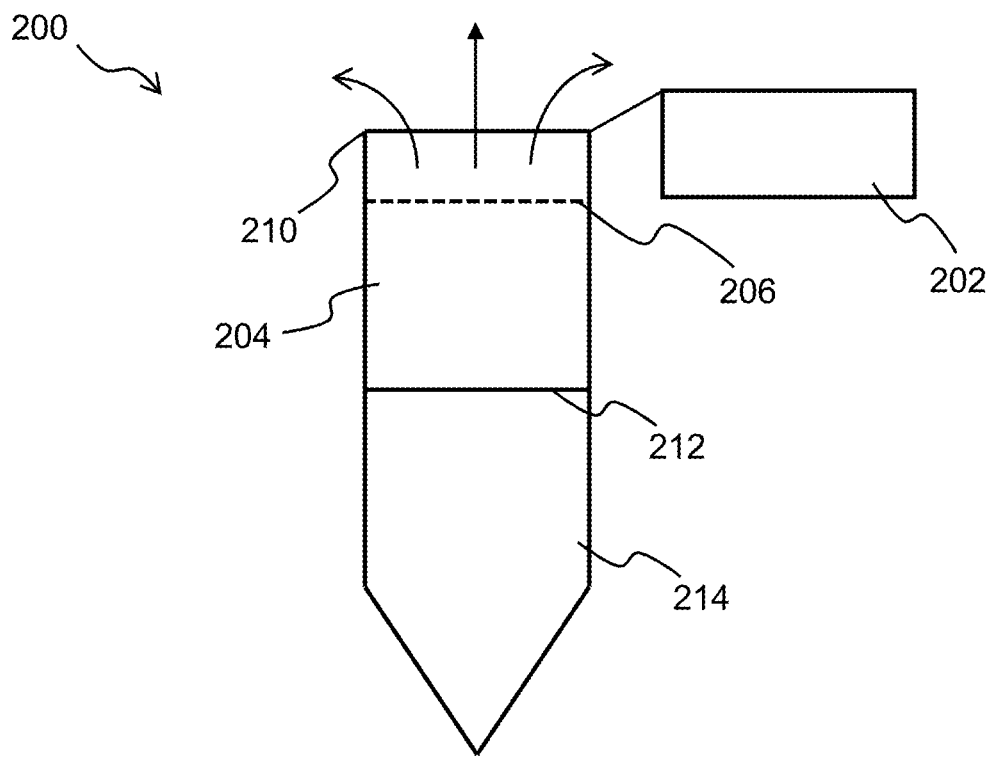
FIG. 7A is a side view of a vertical container with a membrane inserted in the upper portion of the container body according to an embodiment of the disclosure.
Figure 7B:
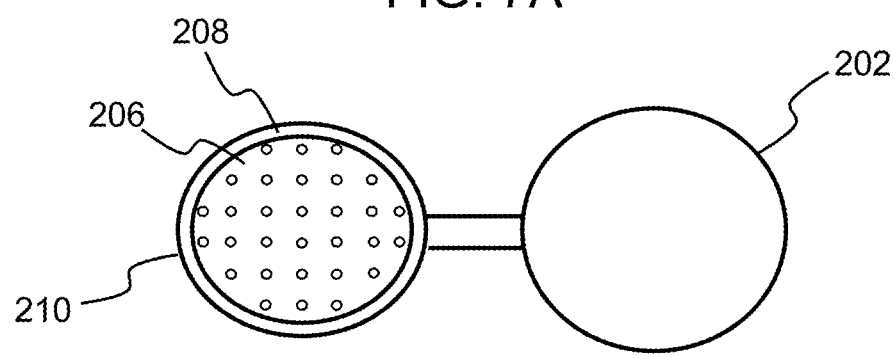
FIG. 7B is a top view of the vertical container and membrane of FIG. 7A.

As shown in FIGS. 7A and 7B, container 200 includes body 204 and cap 202. Frame 208 (shown in FIG. 7B) of membrane 206 can be inserted into the upper portion of body 204 below opening 210 and above fill line 212 of heat-sensitive substance 214. Frame 208 can be inserted via friction fit, snapping in, or screwing on. Prior to insertion of membrane 206, the interior of body 204 is filled with heat-sensitive substance 214 which subsequently undergoes freeze-drying. In some embodiments, after lyophilization, body 204 can be sealed with cap 202.

Figure 8A:
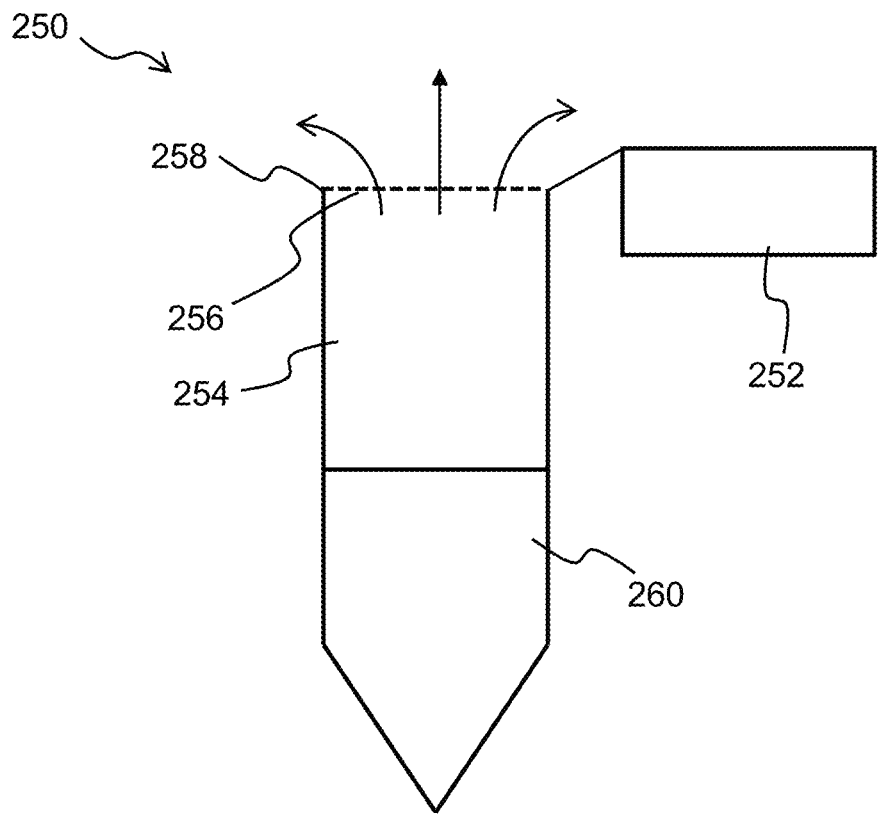
FIG. 8A is a side view of a vertical container with a membrane disposed over the opening of the container body according to an embodiment of the disclosure.
Figure 8B:
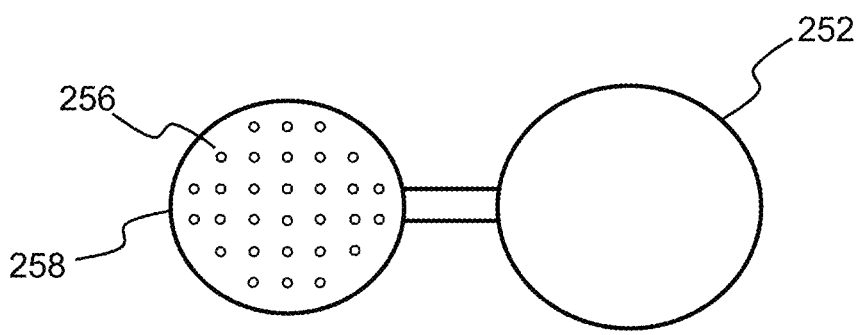
FIG. 8B is a top view of the vertical container and membrane of FIG. 8A.

FIGS. 8A and 8B illustrate container 250 that includes body 254 and cap 252. Membrane 256 can be snapped or screwed onto the top of body 254 such that the membrane covers opening 258. In some embodiments, membrane 256 can be secured over opening 258 via an adhesive band (not shown). Prior to attachment of membrane 256 to opening 258, the interior of body 254 is filled with heat-sensitive substance 260. In some embodiments, after lyophilization, body 254 can be sealed with cap 252.

Figures 9A, 9B:
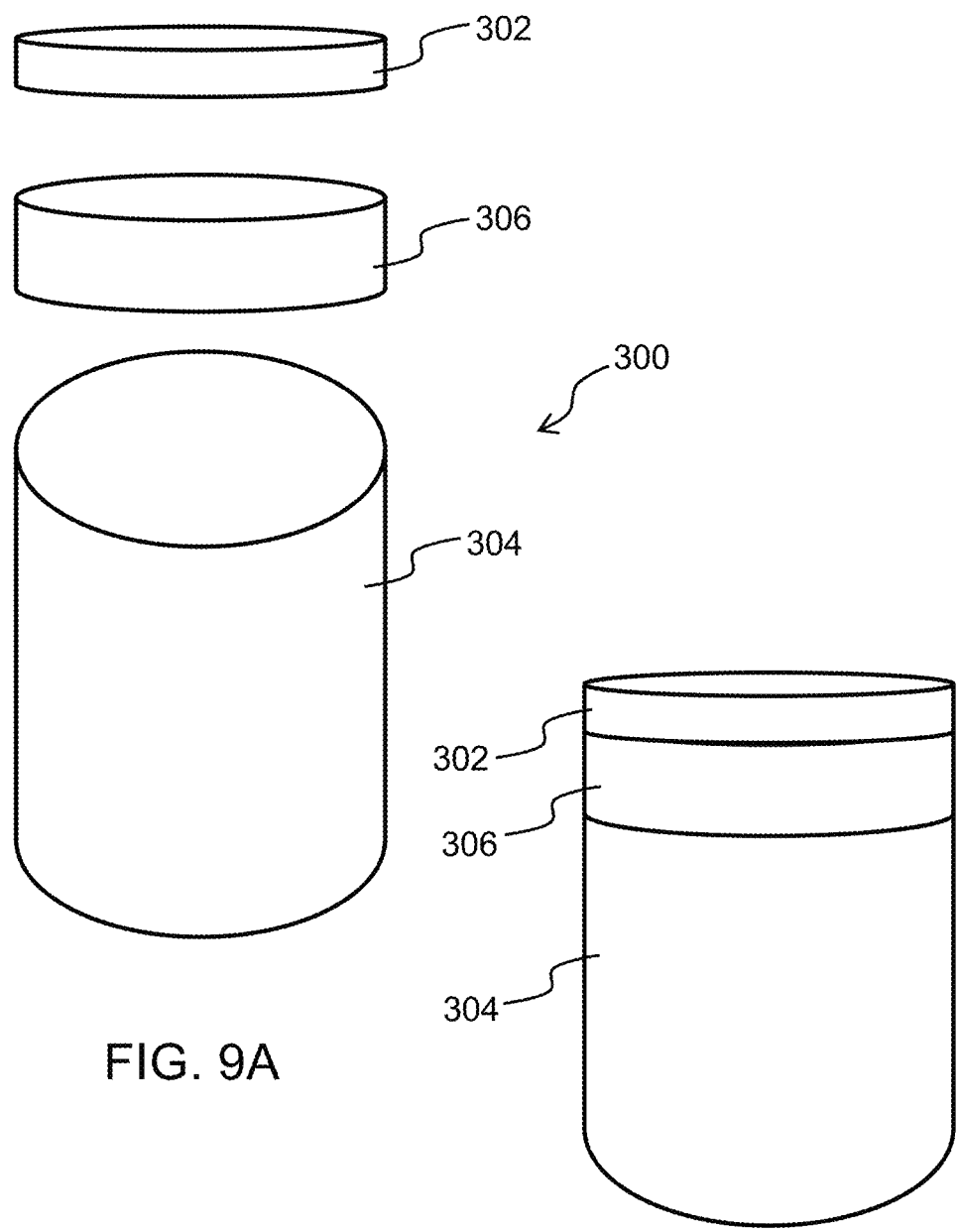
FIG. 9A is an exploded, perspective view of a vertical container with a collar according to an embodiment of the disclosure.
FIG. 9B is a perspective, side view of the vertical container of FIG. 9A.

FIGS. 9A and 9B illustrate another embodiment of a vertical container that can be used with a membrane. Container 300 includes lid 302 and body 304 with removable collar 306 disposed therebetween. In these embodiments, a membrane can be inserted into collar 306. Following lyophilization of a heat-sensitive substance, the container can be sealed with lid 302.

Figure 10:
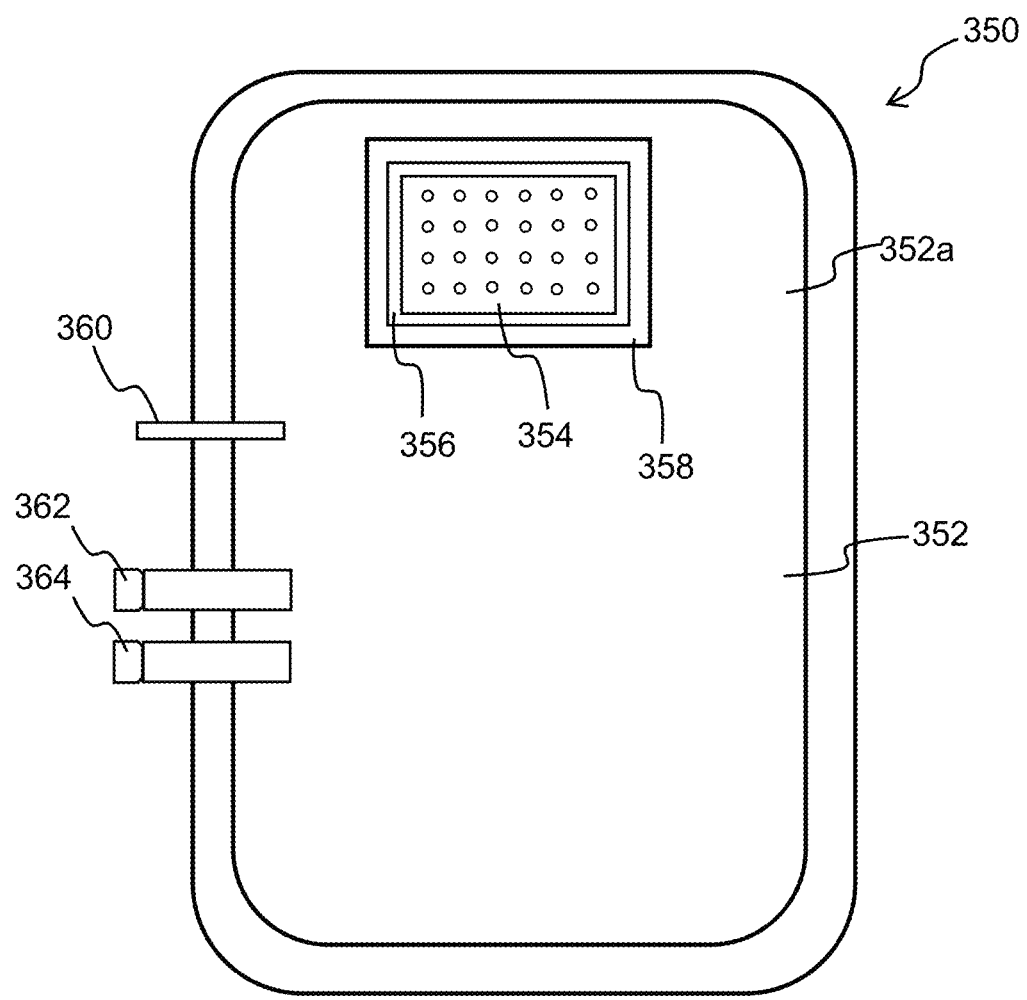
FIG. 10 is a front view of a flexible, vertical container with a membrane according to an embodiment of the disclosure.

FIG. 10 illustrates an embodiment of a flexible container that can house a heat-sensitive substance for freeze-drying. Flexible container 350 includes front side or wall 352 having a membrane disposed in upper portion 352a and a back side or wall (not shown). Flexible container 350 can be held in an upright position, such that the membrane faces outward, by a tray or holder (not shown) to support the front and back walls. Flexible container 350 can be made of suitable, sealable materials including, but not limited to, medical grade plastic such as PVC, polypropylene, or high density polypropylene.

Membrane 354 disposed in upper portion 352a vents air or solvent vapor out of flexible container 350 during freeze-drying and prevents, or at least reduces, liquid and/or contaminant passage into the container. Membrane frame 356 is coupled to the perimeter of and provides support to the membrane. Membrane frame 356 can mate with receiving frame 358 extending through front side 352 of the container, thereby attaching the membrane to the container. In some embodiments, container 350 includes more than one membrane. For example, the container could include a membrane on the front and back walls.

Flexible container 350 includes at least one material entry port 360 for receiving a heat-sensitive substance, with or without the presence of additives, modifiers, or preservatives, into the interior of the container. Entry port 360 can be positioned below membrane 354 so as to prevent the membrane from collecting moisture or becoming wet when the heat-sensitive substance is introduced into the container. Flexible container 350 can also include reconstitution port 362 and/or application port 364 extending through the lower portion of the container. Ports 362 and 364 allow for aseptic introduction of a reconstitution solution, such as water or saline, and subsequent administration of the reconstituted product to a patient.

In particular embodiments, flexible container 350 is used to receive, freeze-dry, store, reconstitute, and administer biological materials such as blood plasma. In these embodiments, flexible container 350 functions as a blood plasma unit, including approximately 250-270 mL of blood plasma from a single donor or pooled donors. The blood plasma unit can be dried such that its moisture content is below 5% by weight.

Once the heat-sensitive material is lyophilized in any of the vertical containers disclosed herein, the container can be sealed and/or stored at conditions (temperature, humidity, light exposure, etc.) appropriate for the freeze-dried material. In certain embodiments, the cap and/or membrane can be removed (e.g., cut off) and the flexible container sealed at or below the former location of the cap and/or membrane. Lyophilized containers can be bar coded and tagged with appropriate identifying information, storage conditions, and/or reconstitution and administration instructions. The bar coding and tagging can, for example, reflect biological material identification, including blood plasma source, blood type, date of collection, etc. To keep track of such information, the bar code printed on the identification tag can be scanned and labels with associated information can be printed. The printed labels can be placed on an external foil containment pouch and a final packaging, for example. The lyophilized material can then be reconstituted with an appropriate solvent and used. In some embodiments, use includes administering the reconstituted material to a human or animal patient.

Figure 11:
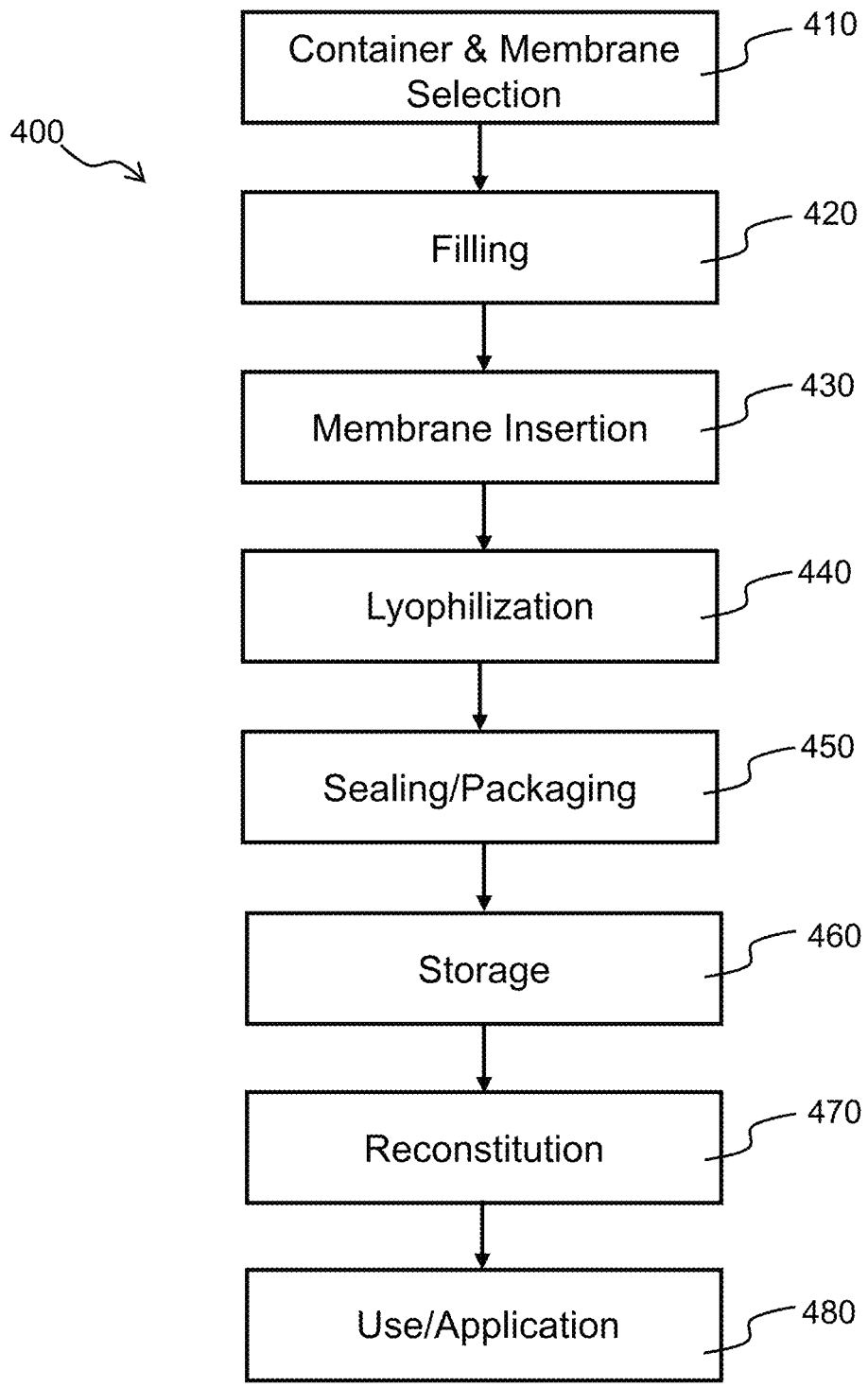
FIG. 11 is a flowchart of a method for freeze-drying a heat-sensitive substance in a vertical container with a membrane according to an embodiment of the disclosure.

FIG. 11 illustrates a method for freeze-drying and reconstituting a heat-sensitive substance using a container disclosed herein. Container & Membrane Selection Stage 410 of Method 400 includes selecting a container and accompanying permeable membrane for a particular heat-sensitive substance. Factors that can influence container and membrane selection include, but are not limited to:
chemical and physical properties of the heat-sensitive substance;
quantity of the heat-sensitive substance;
lyophilization protocol;
conditions of freeze-drying environment and/or equipment;
projected storage duration;
storage conditions (humidity, temperature, light exposure, etc.);
reconstitution volume;
reconstitution solvent; and/or
intended use or application.

Once a container and membrane are selected, the container is filled with the heat-sensitive substance in Filling Stage 420. The membrane is then introduced to the body of the container as disclosed herein in Membrane Insertion Stage 430. Alternatively, when the membrane is integrated into a cap, the cap is inserted onto the body of the filled container.

During Lyophilization Stage 440, the container is held in a vertical position, by self-standing or through the use of a tray or holder, such that the membrane is in an upward-facing position. This membrane placement can allow for controlled and consistent conduction of air and/or solvent vapor out of the container through the membrane. The heat-sensitive substance then undergoes lyophilization. The membrane also prevents, or at least reduces, entry of contaminants into the container during lyophilization. The parameters of the lyophilization cycle or protocol and the equipment used can be selected based on the identity of the heat-sensitive substance and its intended downstream use. For example, if the heat-sensitive substance is a pharmacological compound or biological material that will be administered to a patient, lyophilization can be performed under appropriate regulatory conditions.

During Sealing/Packaging Stage 450, the lyophilized container is sealed and optionally packaged. In some embodiments, the membrane provides a sealing mechanism for preventing, or at least reducing, entry of liquids and/or contaminants during storage. In some embodiments, Sealing/Packaging Stage 450 can include barcoding and tagging the container.

In Storage Stage 460, the lyophilized container is stored at conditions appropriate for the freeze-dried material and its intended storage length.

Once a lyophilized container is selected for use, it is removed from storage and reconstituted with an appropriate solvent in Reconstitution Stage 470. For example, if the freeze-dried material is a drug that will subsequently be administered to a patient, the material can be reconstituted with an appropriate volume of sterile saline to reach the target therapeutic concentration for drug delivery. In some embodiments, a syringe carrying a preferred solvent, can be used to pierce the membrane, disposed in the lid or body of the container, and deliver the solvent to reconstitute the freeze-dried material.

In Use/Application Stage 480, the reconstituted material is used for a particular application. In some embodiments, during Use/Application Stage 480, the reconstituted material is administered to a human or animal patient via infusion, injection, inhalation, or oral administration.

While particular elements, embodiments and applications of the present invention have been shown and described, it will be understood that the invention is not limited thereto since modifications can be made by those skilled in the art without departing from the scope of the present disclosure, particularly in light of the foregoing teachings.

We claim:

1. A system comprising:
    an upright container comprising a body defined by an upper portion, with an opening formed therein, and a lower portion;
    a removable cap sealably attached to the upper portion of the body and configured to cover the opening; and
    a permeable membrane configured to transmit air or solvent vapor out of the upright container while resisting liquid or contaminant passage into the upright container, the membrane disposed above a fill line of the upright container.

2. The system of claim 1, further comprising a membrane frame coupled to the perimeter of the membrane.

3. The system of claim 2, wherein the membrane frame attaches to the upper portion of the body such that the membrane covers the opening of the upright container.

4. The system of claim 3, wherein the membrane frame attaches to the top of the body via a lip and groove mechanism or threads.

5. The system of claim 2, wherein the membrane frame is inserted into and attached to the upper portion of the body and transmits air or solvent vapor out of the upright container while resisting liquid or contaminant passage into the upright container when the cap is removed from the upper body.

6. The system of claim 5, wherein the membrane frame is inserted into and attached to the upper portion of the body via friction fit, a lip and groove mechanism, or threads.

7. The system of claim 2, wherein the membrane frame is inserted into and attached to the cap of the upright container and transmits air or solvent vapor out of the upright container while resisting liquid or contaminant passage into the upright container when the cap is attached to the upper body.

8. The system of claim 7, wherein the membrane frame is inserted into and attached to the cap via friction fit, a lip and groove mechanism, or threads.

9. The system of claim 1, wherein the upright container is a glass lyophilization vial.

10. The system of claim 1, wherein the upright container is a conical centrifuge tube.

11. The system of claim 1, wherein the upright container is a microcentrifuge tube.

12. The system of claim 1, wherein the cap is a snap cap closure.

13. The system of claim 1, wherein the cap is a plug or stopper.

14. The system of claim 1, further comprising a heat-sensitive substance.

15. The system of claim 14, wherein the heat-sensitive substance is a biological material.

16. The system of claim 14, wherein the heat-sensitive substance is a pharmaceutical formulation.

17. The system of claim 14, wherein the heat-sensitive substance is a therapeutic product.

18. The system of claim 1, wherein the upright container is a blood collection tube.

19. The system of claim 1, wherein the cap is a screw cap.

* * * * *